United States Patent [19]

Zaosheng

[11] Patent Number: 5,233,092

[45] Date of Patent: Aug. 3, 1993

[54] DIPHOSPHONATE COMPOUNDS, THEIR PREPARATION AND APPLICATION

[76] Inventor: Xiao Zaosheng, Balin Petro-Chemical Company, Yueyang, Hunan, China

[21] Appl. No.: 822,385

[22] Filed: Jan. 17, 1992

Related U.S. Application Data

[62] Division of Ser. No. 592,166, Oct. 3, 1990, abandoned.

[30] Foreign Application Priority Data

Nov. 6, 1989 [JP] Japan .................................. 1-108289

[51] Int. Cl.$^5$ ............................................. C07C 45/33
[52] U.S. Cl. ................................... 568/360; 568/320; 568/399; 568/815; 568/836; 568/357
[58] Field of Search ................ 558/163; 568/357, 360, 568/399, 815, 836, 320

[56] References Cited

U.S. PATENT DOCUMENTS 3,538,196 11/1970 Baranauckas et al. .............. 558/163

FOREIGN PATENT DOCUMENTS 1035960 10/1989 China .................................. 558/163

*Primary Examiner*—James H. Reamer
*Attorney, Agent, or Firm*—Pennie & Edmonds

[57] ABSTRACT

The invention relates to a new compound of the formular (1):

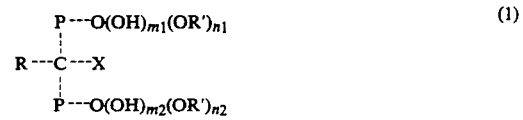

wherein $m_1=0$, 1 or 2, $m_2=0$, 1 or 2, $m_1$ and $m_2$ are not to be simultaneously 0 or simultaneously 2; $n_1=2-m_1$, $n_2=2-m_2$; R=either H or alkyl with 1 to 8 carbon atoms, R'=alkyl with 1 through 18 carbon atoms, and X=H or OH.

The invention also relates to the preparation thereof, the compositions containing them and the application in catalysis of oxidation of hydrocarbons, particularly in catalysis of oxidation of cyclohexane.

7 Claims, No Drawings

DIPHOSPHONATE COMPOUNDS, THEIR PREPARATION AND APPLICATION

This is a division of application Ser. No. 07/592,166, filed Oct. 3, 1990 now abandoned.

The present invention relates to new diphosphonate compounds.

More particularly, the present invention relates to new kinds of diphosphonate compounds, their preparation process, compositions containing them and their application.

Accordingly, one of the purposes of the present invention is to provide new and useful diphosphonate compounds.

Another purpose of the present invention is to provide a process for making the said diphosphonate compounds.

Yet another purpose of the present invention is to provide compositions containing the diphosphonate compounds for catalysis.

A further purpose of the present invention is to provide application of the said diphosphonate compounds and compositions containing them for catalysis in oxidation of hydrocarbons, the oxidation of cyclohexane, in particular, etc.

The diphosphonate compounds of present invention are novel and may be designated by the following general formula (1),

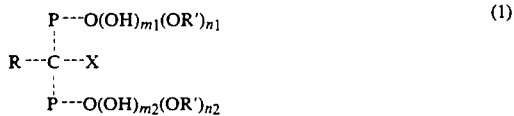
(1)

wherein m1=0, 1 or 2, m2=0, 1 or 2, with the constraint that m1 and m2 are not to be simultaneously 0 or simultaneously 2; n1=2−m1, n2=2−m2; R=either H or alkyl with 1 to 8 carbon atoms, R'=alkyl with 1 through 18 carbon atoms, and X=H or OH.

The compounds of this invention may be mon-, di-, or tri-ester of diphosphonates, or a mixture of the three, with the di-ester of diphosphanates being the preferred product.

The "R" in the formula (1) is preferred to be H or a linear/branched alkyl with 1 through 6 carbon atoms, and more preferred to be an alkyl with 1 through 3 carbon atoms, methyl for instance.

The "R'" in the formula (1) is preferably a linear/branched alkyl with 6 through 14 carbon atoms, and even more preferably, a branched alkyl with 8 to 12 carbon atoms, like 2-ethyl-hexyl.

The "X" in the general formula (1) is preferably OH.

A process for producing the said diphosphonate compounds of the general formula (1),

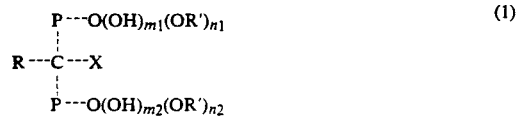
(1)

wherein the definitions of m1, m2, n1, n2, R, R' and X are the same as above, consists of the steps of dissolving in certain solvent the solid phosphinic acids designated by the general formula (2),

(2)

wherein R and X are defined as in the formula (1), and adding under normal pressure the solution of diphosphinic acids thus obtained into an alcohol designated by the general formula (3),

R'OH (3)

wherein the R' is defined as in the formula (1), where esterification reaction will take place and the substances designated by the general formula (1) will be obtained.

The diphosphinic acids of the formula (2) are preferred to be those wherein R is H or an alkyl with 1 through 6 carbon atoms and more preferred to be those wherein R is an alkyl with 1 through 3 carbon atoms, such as methyl, and X is OH. The alcohols of the formula (3) are preferred to be those wherein R' is an alkyl having from 6 to 14 carbon atoms and more preferred to be those wherein R' is a branched alkyl having 8 through 12 carbon atoms, for example, 2-ethyl hexyl. Both the diphosphinic acids of the formula (2) and the alcohols of the formula (3) are available on the markets.

The esterification temperature may range from 150° C. to 200° C., preferably from 160° C. to 170° C.

The solvent for dissolving the diphosphinic acids may be selected from methanol, ethanol and water, with water being the preferred.

It is recommended that the diphosphinic acids be poured into an alcohol, under stirring, gently in order to raise the yield.

Another aspect of the present invention relates to a composition containing the diphosphonates of this invention.

The composition is composed of the diphosphonate compounds of this invention and one or several transitional metal salts, of which molar ratio ranges between 1:1–20, preferably 1:3–10.

The transitional metals thereof may be selected from the salts of cobalt, copper, manganese, vanadium, chromium and molybdenum, or their mixture, with cobalt as the one preferred.

The composition may be prepared by simply mixing the diphosphonate compounds with the transitional metal salts.

The compounds of the present invention may be used alone or in the form of composition for oxidation of hydrocarbons such as the catalyzed oxidation of cyclohexane, oxidations of p-xylene and of paraffins.

There are primarily two processes hitherto known in industries for oxidation of hydrocarbons: organic salt-catalyzed oxidation in liquid phase and non-catalyzed oxidation. The diphosphonate compounds of the present invention will, when used, improve both processes.

In the case of non-catalyzed process, the diphosphonate compounds of the present invention, when added, will curb the side-reactions and raise the yield accordingly.

In the case of catalyzed process, adding of the compounds of the present invention improves the catalyzing activity of relevant metal ions and lessens deep oxidation, preventing cake-forming and hence extending continuous production period, and as a result, the yield goes up.

The amount of the compounds of the present invention added as a co-catalyst may vary from 0.01 to 10 ppm and preferably from 0.05 to 5 ppm.

The composition of the present invention may also be directly added as a catalyst in the case of catalyzed process, the concentration of which may range from 0.1 to 100 ppm per total feeds, preferably from 0.5 to 10 ppm.

The compounds of the present invention and composition containing them as catalysts are especially suitable for commercial operations of the cyclohexane oxidation. With the current use of conventional cobalt-based catalyst, the molar yield is always below 80 per cent and cake-forming severe. Moreover, when pyrophosphate is spread over the walls, the production can run only about two months before being forced to shut down for cleaning cake-deposits, which causes not only interruption of production, but serere environmental pollution as well.

In contrast, without the need for changing in process parameters of cobalt catalyzing and equipment, the diphosphonate compounds of the present invention is capable of improving the catalyst activity of cobalt ion for the oxidation of cyclohexane, lessening deep oxidations, stopping the heavy build up of cakes and equipment plug, extending the period of non-stop running and raising the yields for alcohols and ketones.

In the case of the cyclohexane oxidation, the dosage of the compounds of the present invention may vary from 0.01 to 10 ppm and preferably from 0.5 to 5 ppm; whereas when the composition of the present invention is used, the dosage ranges from 0.1 to 100 ppm, preferably from 0.5 to 10 ppm.

In addition, the diphosphonate compounds of the present invention may also be used as a complex-extracting agent for metal ions and coagulant for epoxy resin.

The following are examples which are quoted here merely to illustrate some aspects of the present invention and they by no means limit the scope of this invention.

EXAMPLE 1

3,500 ml of 2-ethyl hexanol was poured into a 5,000 ml three-necked flask heated with hot plate at the bottom and stirred by bubbling nitrogen through the contents. At the top of the flask, a decanter and a condensing coil of ball type were mounted with cooling water circulating through the jacket of the coil. When the temperature reached 160° C., HEDP (i.e. 1-hydroxy-ethylidene-1,1-diphosphinic acid rs, similarly hereinafter) solution was gently added. While both 2-ethyl hexanol and water were boiling (azeotropism), the vapor flowed through the coil where it condensed, and into the decanter where water was taken out of the system from the bottom and the top layer, 2-ethyl hexanol condensate recycled back to the reactor. The amount of solid HEDP in the solution that was added into the system for each batch was 1,100 g. The feeding had lasted for some 2 hours before the system was held under reflux for 30 minutes until all the resultant water was bled off. After reaction, about 4,000 ml crude product was obtained in the flask. When cooled down, the product so obtained was rinsed with equal amount of water, and 4,000 ml of cyclohexane was added. Having settled, the contents split into two layers: in the bottom one there was a small amount of unreacted diphosphinic acids and sulfuric acid (catalyst); the top layer—an oil layer, was then distilled in vacuum where water, cyclohexane and 2-ethyl hexanol were removed from the top, and at the bottom, about 2,000 g of product, was obtained.

The melting point of the product is −39° C., and the decomposition temperature—215° C. The results of a series of tests using field-decomposition mass spectrum (FDMS), infra-red spectrum (IR) and nuclear magnetism resonance (NMR), etc. proved that the principal component was di-2-ethyl-hexyl 1-hydroxy-ethylidene-1,1-diphosphonate ester with only small amounts of mono-2-ethyl-hexyl 1-hydroxy-ethylidene-1,1-diphosphonate ester, tri-2-ethyl-hexyl 1-hydroxy-ethylidene-1,1-diphosphonate ester, and 2-ethyl hexanol as impurities. The di-2-ethyl-hexyl 1-hydroxy-ethylidene-1,1-diphosphonate ester has been proven to be a new compound (see below).

IR: 1017 cm, 1218 cm, 1380 cm, 1463 cm etc.
NMR: 0.83 ppm, 1.24 ppm, 3.95 ppm.
FDMS m/Z: 341 [M1+Na], 453 [M2+Na], 565 [M3+Na], wherein
M1=mono-2-ethyl-hexyl 1-hydroxy-ethylidene-1,1-diphosphonate ester
M2=di-2-ethyl-hexyl 1-hydroxy-ethylidene-1,1-diphosphonate ester
M3=tri-2-ethyl-hexyl 1-hydroxy-ethylidene-1,1-diphosphonate ester

EXAMPLE 2

As a comparative case with example 1, 3,500 ml of 2-ethyl hexanol and 1,100 g of solid HEDP were added into a 5,000 ml three-necked flask heated with hot plate at the bottom and stirred by bubbling nitrogen through the contents. At the top of the flask, a decanter and a condensing coil of ball type were mounted with cooling water circulating through the jacket of the coil. When the temperature reached between 130° and 200° C., the liquid began to boil and reaction started, yet with very slow rate of esterification. The results showed that only a small amount of HEDP esters were yielded. It is believed that the predominant reaction was, in fact, the dehydration of 2-ethyl hexanol which caused formation of a great amount of 2-ethyl hexene.

EXAMPLE 3

Also taken as a comparative case with example 1, 3,500 ml of light oil which had been taken as a by-product from the process of an oxidation of cyclohexane for producing cyclohexanone, and mainly contained esterification-capable components including cyclopentanol, n-pentanol and cyclohexanol was poured into a 5,000 ml three-necked flask heated with hot plate at the bottom and stirred by bubbling nitrogen through the contents. At the top of the flask, a water decanter and a condensing coil of ball type were mounted with cooling water circulating through the jacket of the coil. When the temperature reached 140° C. and the liquid began to boil, HEDP dissolved in water was gently added. While both the light oil and water were boiling (azeotropism), the vapor flowed through the coil where it condensed, and into the decanter where water was taken out of the system from the bottom and the top layer—the light oil condensate recycled back to the reactor. The amount of solid HEDP in the solution that was added into the system for each batch was 200 g. The feeding had lasted for some 2 hours before the system was held under reflux for 30 minutes until all the resultant water was bled off. After reaction, about 3,500 ml crude product was obtained in the flask. When cooled down, the product so obtained was rinsed with the equal amount of water, and 3,500 ml of cyclohexane was added. Having settled, the contents split into two layers: in the bottom one there was a large amount of unreacted diphosphinic acid and a little sulfuric acid (catalyst); the top layer—an oil layer, was then distilled in vacuum where water, cyclohexane and light oil were removed from the top and at the bottom, only tiny amount of pentyl HEDP esters (approx. 10 g), the product, was obtained. The yield of useful diphosphonates was very poor.

EXAMPLE 4

3,500 ml of lauric alcohol was poured into a 5,000 ml three-necked flask heated with hot plate at the bottom and stirred by bubbling nitrogen through the contents. At the top of the flask, a decanter and a condensing coil of ball type were mounted with cooling water circulating through the jacket of the coil. When the temperature reached 160° C. first 50 ml of p-xylene was added and then HBDP (1-hydroxy-butenylidene-1,1-diphosphinic acid was gently added. While the lauric alcohol, PX and water began boiling (azeotropism), the vapor flowed through the coil where it condensed, and into the decanter where water was taken out of the system from the bottom and the top layer—the lauric alcohol and PX condensate recycled back to the reactor. The amount of solid HBDP in the solution that was added into the system for each batch was 1,500 g. The crude product was rinsed, distilled and finally, 2,400 g product, di-lauric 1-hydroxy-butenylidene-1,1-diphosphonate ester was obtained by the following equation:

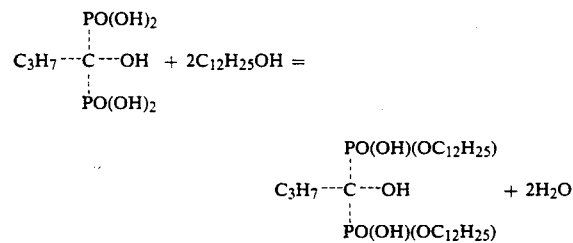

EXAMPLE 5

100 ml of benzene was added to a 250 ml separating funnel and then 1 g of cobalt cycloalkanoates was added, which was evenly suspended in the benzin phase and the cobalt ions were extracted into water phase later on after 100 ml of 2% solution of hexane diacid was added. At this point, 1 g of di-2-ethyl-hexane HEDP ester was added, and the cobalt ions in the water phase below were extracted back to the oil layer above.

EXAMPLE 6

50 g of epoxy resin of general purpose, while being stirred, was mixed with 5 g of dilauric HBDP ester. After being heated for 40 minutes at a temperature between 160° and 200° C., the resin was perfectly fixed and molded, with all the targets meeting the standards upon tests.

EXAMPLE 7

This is a comparative case with example 8 that follows, in an industrial unit for producing 8,000 t/y of cyclohexanone by cobalt-catalyzed oxidation of cyclohexane, sodium pyrophosphate was spread over the walls of reactors for deactivation. The feed of cyclohexane was 36 m$^3$/h; and air flow 2,100 Nm$^3$/h. Cobalt salt in the form of cycloalkanoates in cyclohexane solution was fed into the system continuously; the concentration of cobalt ions in the oxidation system was controlled at 0.26 ppm by weight, or 2 Kg of cobalt cycloalkanoates (about 8% of cobalt ions) mixed in 2 m$^3$ of cyclohexane each day. The amount of prepared 2 m$^3$ of cobalt salt in cyclohexane solution was metered and fed out by metering pumps into No. 1 oxidation reactor continuously at a fixed rate over 24 hours. The system pressure was controlled at 1 MPa.g.; reaction temperature—154+/−2° C. the process of oxidation of cyclohexane went smoothly. The off-gas from the oxidation contained 2.5% of oxygen, when sampled with a glass sampling bottle. By visual exam, the samples looked turbid, with a small amount of yellow brown liquid at the bottom and some particles of the same color sticking to the walls of the bottle. After subsequent processes: saponification, distillation of oxidized products, and dehydrogenation of cyclohexanol, etc., an average output of 27.1 t/d of cyclohexanone was obtained at a consumption of cyclohexane—33.1 t/d. After about 2 months continuous running this way, the operation was forced to shut down for 48 hours to clean the system before resuming, because of heavy deposits that occurred inside the reactors and connecting piping, causing eventually system plugged. During the cleaning, the reactors and piping were flashed with a large amount of soda water combined with manual cleaning of the deposits.

EXAMPLE 8

It is a case adopting the composition as a catalyst in an industrial unit for producing 8,000 t/y of cyclohexanone by cobalt-catalyzed oxidation of cyclohexane, the same unit as of example 7, but without using sodium pyrophosphate as a deactivator. The feed of cyclohexane was still 36 m$^3$/h; and air flow 2,100 Nm$^3$/h. Cobalt salt in the form of cycloalkanoates mixed with diphosphonates in cyclohexane solution was fed into the system continuously; the concentration of cobalt ions in the oxidation system was controlled at 0.26 ppm by weight, and the molar ratio between cobalt ions and the diphosphonates was 7:1, or 2 Kg of cobalt cycloalkanoates (about 8% of cobalt ions), together with 150 ml of the diphosphonates, mainly di-2-ethyl-hexane HEDP ester mixed in 2 m$^3$ of cyclohexane each day. The amount of prepared 2 m$^3$ of cobalt salt/diphosphonates in cyclohexane solution was metered and fed out by metering pumps into No. 1 oxidation reactor continuously at a fixed rate over 24 hours. The system pressure was controlled at 1 MPa.g.; reaction temperature—154+/−2° C. The process of oxidation of cyclohexane went smoothly. The off-gas from the oxidation contained 2.0% of oxygen, when sampled with a glass sampling bottle. By visual exam, the samples looked clear and bright, with a small amount of colorless liquid at the bottom which was proven to be an acid water, and only when oxidation conversion rate went high, some white particles, crystal hexane diacid, could be found sticking to the walls of the bottle. After subsequent processes: saponification, distillation of oxidized products, and dehydrogenation of cyclohexanol, etc., an average output of 30.2 t/d of cyclohexanone was obtained at a consumption of 34.7 t/d of cyclohexane.

When compared with example 7, the output per unit time went up by 10% and total yield up by 5% respectively. After one year's continuous running this way, there was still no sign of deposits in either reactor or piping. The operation would have been kept going, had there not been an annual scheduled shut down for maintenance. When opened without any cleaning, no deposits, what so ever, was found inside the equipment or piping system and the walls inside were shining as they had been originally. It can be ascertained that the unit as it was may be continuously run for at least one year.

EXAMPLE 9

In conventional process of non-catalyzed oxidation of cyclohexane for producing cyclohexanone/cyclohexanol, sodium pyrophosphate is used as a deactivator to spread over the walls of reactors, which will bring in sodium ions which, in turn, will accelerate the side reactions causing poor yield. This time, in the same unit, all process parameters were kept unchanged except that instead of spreading sodium pyrophosphate on the walls, a small amount of diphosphonates, mainly di-2-ethyl-hexane HEDP ester, was continuously fed into No. 1 reactor of the oxidation system, with the concentration of diphosphonates in the reactants controlled at 0.3 ppm by weight; and there was no more deposits in the system. In addition, the oxidation product turned less colored and the side reaction depressed. The result was reflected on 2% increase in the total yield of alcohol/ketone products.

EXAMPLE 10

In conventional processes of paraffin oxidation producing higher alcohols/ketones, for instance, in the process of oxidation of C12 through C18 paraffins for producing C12 through C18 alcohols, the same problems of fouling and plugging in the equipment and piping are also puzzling the normal operation. However, when such an amount of di-2-ethyl-hexane HEDP ester was put into the feed stream that the concentration was kept at around 0.3 ppm by weight, or the molar ratio between catalyst metal ions and diphosphonates at 5 to 1, the paraffin oxidation reactors were free from deposits and the usable product yield went up by 3%.

EXAMPLE 11

In a commercially operated unit for producing 1,000 t/y of p-toluic acid by the oxidation of p-xylene, the same problems of fouling/plugging in equipment/piping exist. Only such an amount of di-2-ethyl-hexane HEDP ester was put into the feed stream that the concentration was kept at anywhere between 0.5 ppm and 3 ppm by weight, while all process/equipment parameters were kept unchanged including cobalt-catalyst concentration, reaction pressure, temperature, feed and air flow, etc., no more deposits was found in the reactor and the total yield of target product, p-toluic acid, went up by 3 percent.

I claim:

1. A method for the transition metal ion salt-catalyzed oxidation in liquid phase or the non-catalyzed oxidation in liquid phase of paraffin, cycloalkane or aralkane hydrocarbons to form alcohols and carbonyl compounds in which the said oxidation is carried out in a reaction system containing from 0.01 to 100 ppm per total feeds of a diphosphonate compound having the following formula:

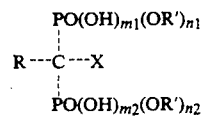

wherein $m_1 = 0, 1$ or $2$; $n_1 = 2 - m_1$; $m_2 = 0, 1$ or $2$; $n_2 = 2 - m_2$; $0 < m_1 + m_2 < 4$; R is H or alkyl having 1–8 carbon atoms; R′ is alkyl having 1–18 carbon atoms; and X is H or OH.

2. The method according to claim 1 wherein R′ is alkyl having 6–14 carbon atoms, and R is H or alkyl having 1–6 carbon atoms.

3. The method according to claim 2 wherein X is OH; R′ is branched alkyl having 8–12 carbon atoms; and R is alkyl having 1–3 carbon atoms.

4. The method according to claim 3 wherein R′ is 2-ethylhexyl; R is methyl; and $m_1$ and $m_2$ are both 1.

5. The method according to claim 1 wherein the hydrocarbon is cyclohexane.

6. The method according to claim 1 wherein the amount of the diphosphonate compound used is from 0.01 to 10 ppm based on the weight of the hydrocarbon in the oxidation reaction system.

7. The method according to claim 1 wherein the amount of the compound used is from 0.05 to 5 ppm.

* * * * *